United States Patent
Ide et al.

[11] Patent Number: 5,308,319
[45] Date of Patent: May 3, 1994

[54] CARDIO ASSIST SYSTEM AND INSERTION DEVICE THEREFOR

[75] Inventors: Hirofumi Ide, Tokyo; Atsushi Yamaguchi, Omiya; Haruhiko Masuda, Fujisawa, all of Japan

[73] Assignee: Sumitmo Bakelite Company Limited, Tokyo, Japan

[21] Appl. No.: 998,768

[22] Filed: Dec. 30, 1992

Related U.S. Application Data

[63] Continuation of Ser. No. 630,623, Dec. 20, 1990, abandoned.

[30] Foreign Application Priority Data

Dec. 28, 1989 [JP] Japan .................................. 1-338140
Nov. 30, 1990 [JP] Japan .................................. 2-329555

[51] Int. Cl.⁵ ............................................. A61N 1/362
[52] U.S. Cl. ........................................ 600/18; 604/53; 604/96; 604/101; 604/280
[58] Field of Search ............... 128/656, 657, 658, 768, 128/786, 772; 604/53, 96, 101, 280; 600/18

[56] References Cited

U.S. PATENT DOCUMENTS

| | | |
|---|---|---|
| 4,625,712 | 12/1986 | Wampler . |
| 4,648,384 | 3/1987 | Schmukler .................... 604/53 X |
| 4,741,328 | 5/1988 | Gabbay . |
| 4,787,892 | 11/1988 | Rosenberg .................... 604/280 X |
| 4,790,331 | 12/1988 | Okada et al. .................. 604/53 X |
| 4,790,825 | 12/1988 | Bernstein et al. . |
| 4,861,330 | 8/1989 | Voss ............................ 604/53 X |

OTHER PUBLICATIONS

Imanishi, Kaoru et al (1989) "Development of a New Circulatory Assist Method with the Combined Effects of Intra-Aortic Balloon Pumping and Counter Pulsation", *Trans. Am. Soc. Artif. Intern. Organs* vol. XXXV, pp. 715-717.

Bregman, D. et al. (1970) "The Effect of Synchronous Undirectional Intra-Aortic Balloon Pumping on Hemodynamics and Coronary Blood Flow in Cardiogenic Shock", *Trans. Amer. Soc. Artif. Int. Organs*, vol. XVI, pp. 439-449.

Primary Examiner—Lee S. Cohen
Assistant Examiner—Brian L. Casler
Attorney, Agent, or Firm—Browdy and Neimark

[57] ABSTRACT

A cardio assist system has an integrated cardio-assist catheter including a multi-lumen tube and an inflatable/deflatable balloon provided on a distal end portion of the tube, a blood pump connected to the proximal end of a main lumen in the catheter, and a balloon driver for supplying and discharging a gas to and from the balloon so as to repeatedly inflate and deflate the balloon. Disclosed also is a device for inserting the cardio assist system to a living body safely, accurately and promptly. A combined use of the cardio assist system and the insertion device enables a quick set up a strong assisted blood circulation system.

4 Claims, 8 Drawing Sheets

CARDIO ASSIST SYSTEM AND INSERTION DEVICE THEREFOR

This application is a continuation of application Ser. No. 07/630,623, filed Dec. 20, 1990, now abandoned.

BACKGROUND OF THE INVENTION

The present invention relates to a cardio assist system suitable for use in medical care of intractable cardiac failure, and also to an insertion device therefor. More particularly, the invention is concerned with the cardio assist system and the insertion device which are always ready for use and highly effective even in cases of emergency.

In recent years, there is a remarkable progress in the field of cardiac surgery and, nowadays, various cardiac diseases which hitherto have been difficult to cure are becoming curable. It is considered that current studies and development in assisted circulation systems, which function in place of failed hearts so as to maintain peripheral circulation and promote recovery of the cardiac function, have made a great contribution to the improvement in the effect of the surgery.

Assisted circulation methods presently available can be sorted into several types: namely, intra-aortic balloon pumping (abbreviated as "IABP"hereinafter), veno-arterial bypass (abbreviated as "VAB"), and left heart bypass which utilizes a ventricular assist device (abbreviated as "VAD").

These known methods, however, have at least one critical shortcoming when considered from the view points of the treatment effect, operability, surgical stress, adaptability to emergency cases and availability of equipment. Thus, the known methods are still unsatisfactory when a patient having an intractable cardiac failure and, hence, requiring very quick treatment is considered. In other words, no method has been proposed which would satisfy all the requirements of elimination of necessity for special equipment, ease and quickness of application in the event of an emergency, minimal surgical procedure and strong assisted circulation.

For instance, IABP does not always provide a good effect when applied to a serious failure such as cardiogenic shock, although it is used widely. VAB also is disadvantageous in that it cannot provide satisfactory assisting effect for the left heart. VAD requires a special equipment and an open-chest operation has to be conducted for installation, thus, failing to cope with an emergency case.

Patients often die due to inferior prognosis caused by a delay in the treatment, even when these methods are fully applied. In some cases, the required assisted circulation cannot be conducted due to unavailability of equipment. Thus, it is a matter of significance to establish a technique which would save the lives of patients which have suffered from such serious diseases.

One of methods which would avert death of patient having intractable cardiac failure is to apply a strong assisted circulation as soon as possible. Thus, it will be a matter of great significance to provide an assisted circulation system which is easy to apply and operate and which is installed by minimal surgical procedure.

SUMMARY OF THE INVENTION

Accordingly, an object of the present invention is to provide a cardio assist system which has a wide adaptability and which produces a large circulation effect.

Another object of the invention is to provide an insertion device which enables a quick and easy installation of the cardio assist system.

The present inventors have made an intense study to develop the cardio assist system which would achieve the above-described objects.

To this end, according to the present invention, the cardio assist system includes an integrated cardio-assist catheter, a balloon driver and a blood pump. Further, according to the present invention, provided is an insertion device suitable for use in combination with such an assisted circulation system.

The invention will be more fully understood from the following description of the preferred embodiment in conjunction with the accompanying drawings.

BRIEF DESCRIPTION OF THE DRAWINGS

FIG. 1A is a sectional view of an integrated cardio-assist catheter of the system, taken along the line 33—33 of FIG. 1;

FIG. 2A is a sectional view of an integrated cardio-assist catheter, taken along the line 33—33 of FIG. 2;

DESCRIPTION OF THE PREFERRED EMBODIMENTS

Figure 1:
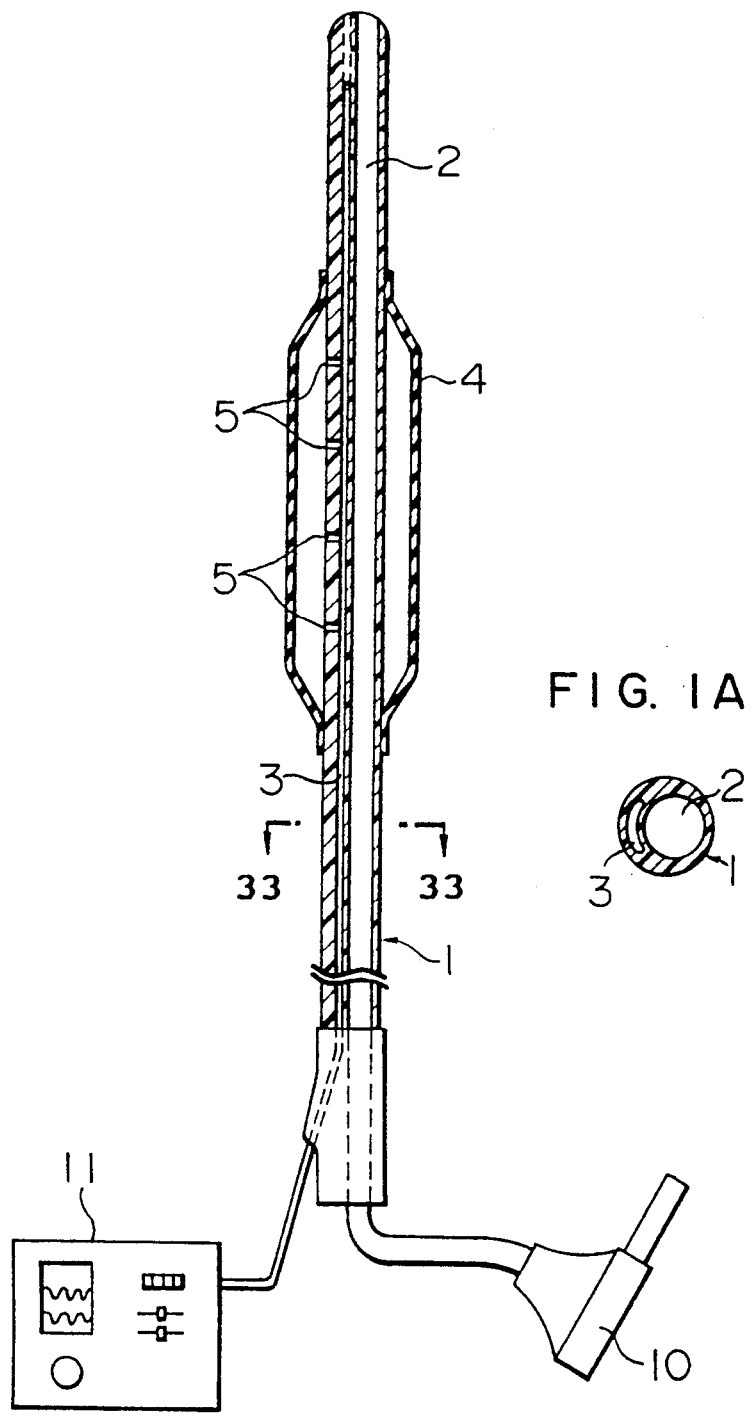
FIG. 1 is a schematic illustration of a cardio assist system according to an embodiment of the invention.

Referring to FIG. 1, a cardio assist system includes an integrated cardio-assist catheter 1. The catheter 1 includes a flexible double lumen tube having a main lumen 2 and a sub-lumen 3 which is sealed at its end, and a balloon 4 air-tightly secured to an outer periphery of the tube. A side port communicating with an interior of the main lumen 2 may be provided in the end of the catheter 1. A plurality of apertures 5 are formed in the peripheral wall of the tube so as to provide a communication between the interior of the sub-lumen 3 and an interior of the balloon 4 so that a drive gas is supplied to the interior of the balloon 4 through the sub-lumen 3. The main lumen 2 and the sub-lumen 3 are separated from each other at a proximal end of the catheter 1. The main lumen 2 is connected to a blood pump 10, while the sub-lumen 3 is connected to a balloon driver 11.

Figure 2:
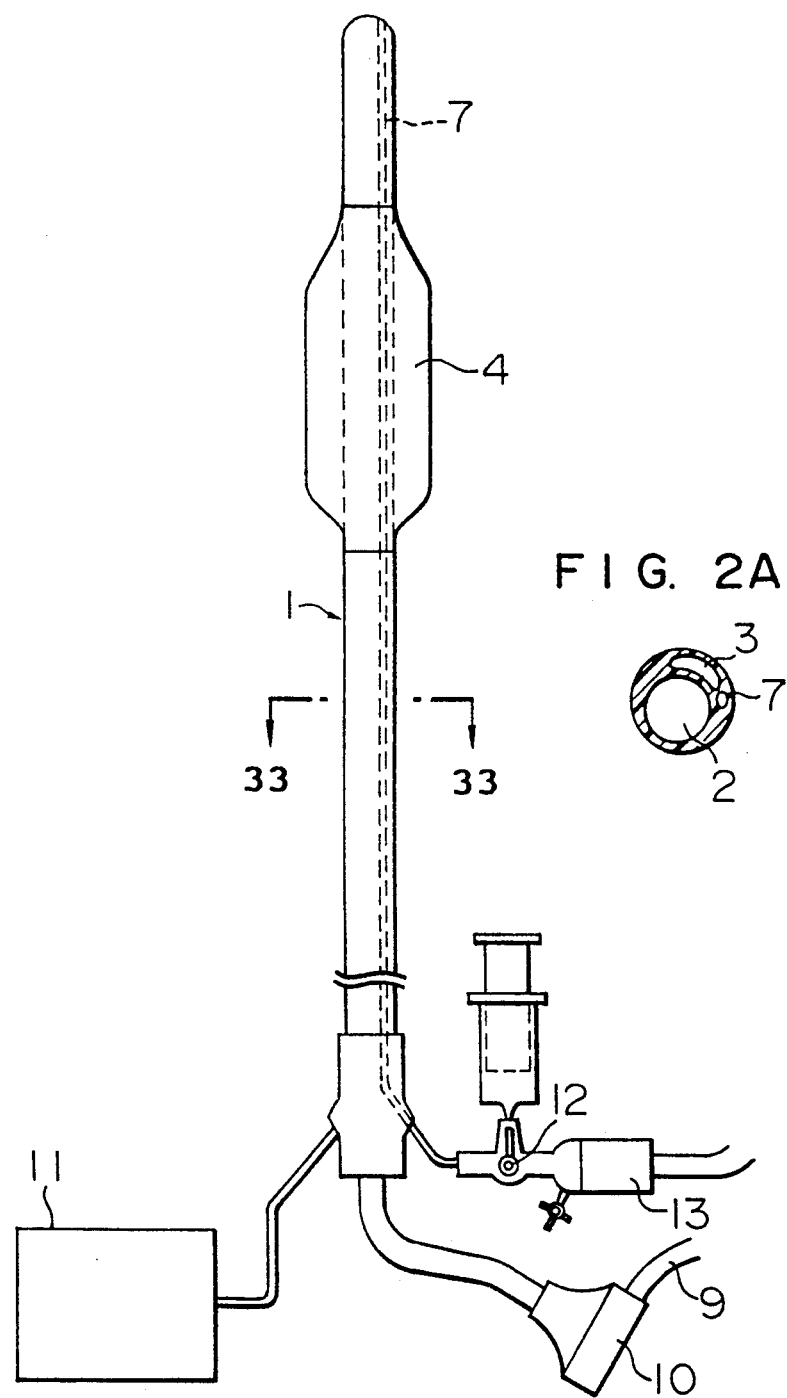
FIG. 2 is a schematic illustration of a cardio assist system according to another embodiment.

A second sub-lumen having a diameter of 1 mm or smaller may be provided as required for the purpose of pressure measurement and injection of a medical fluid, in addition to the sub-lumen 3 which serves as a drive gas supply tube. Such a second sub-lumen 7 for pressure measurement and injection of medical fluid is shown in FIGS. 2 and 2A. A pressure transducer 13 is connected to the proximal end of the second lumen 7 through a 3-way cock 12 which conducts change-over between pressure measurement and injection of medical fluid. The second lumen 7 enables an exact diagnosis of the state of the cardiac failure and quick treatment.

The blood pump 10 may be a roller pump, a centrifugal pump and so on. The centrifugal pump is preferable because of a large flow rate. The balloon driver 11 may be an IABP driver or a VAD driver. IABP drivers, which are used in many hospitals, can be used conveniently. Thus, according to the present invention, a strong assisted circulation can be attained without requiring any specific additional equipment.

Figure 3:
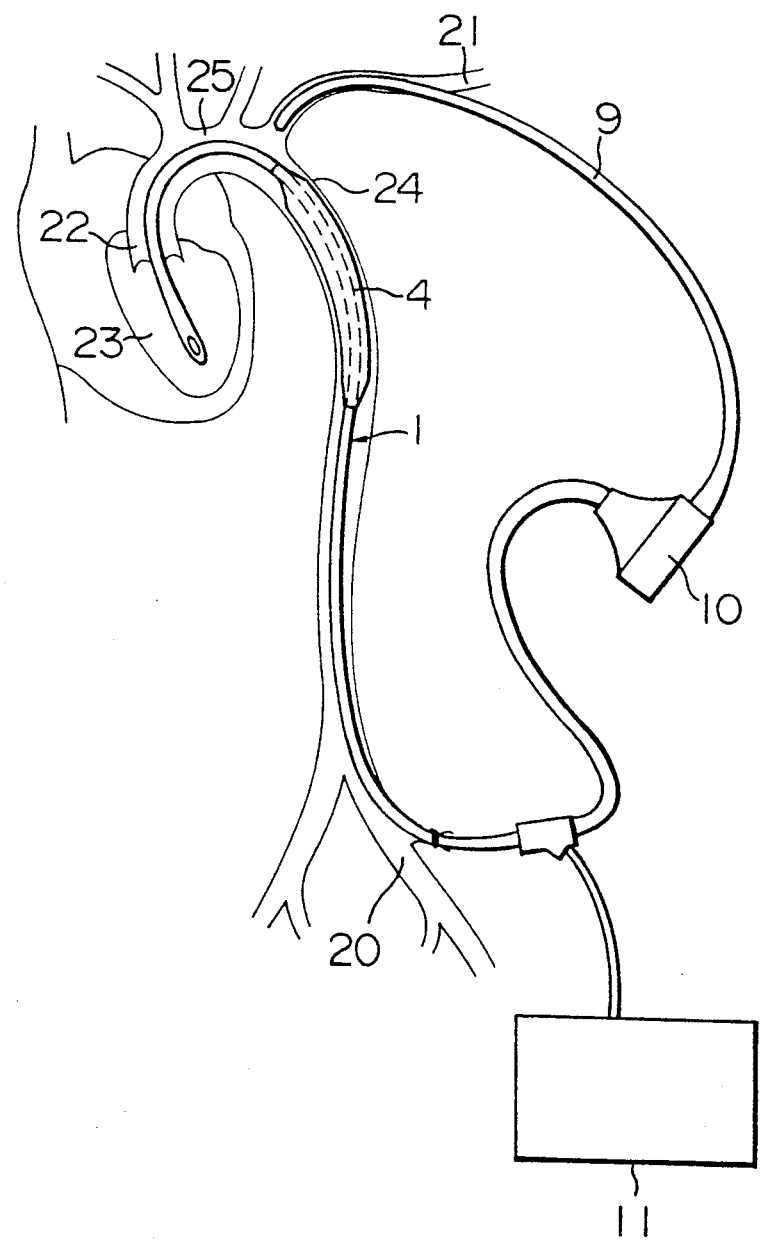
FIGS. 3 to 5 are illustrations of the manner of use of the cardio assist system of the present invention.
Figure 4:
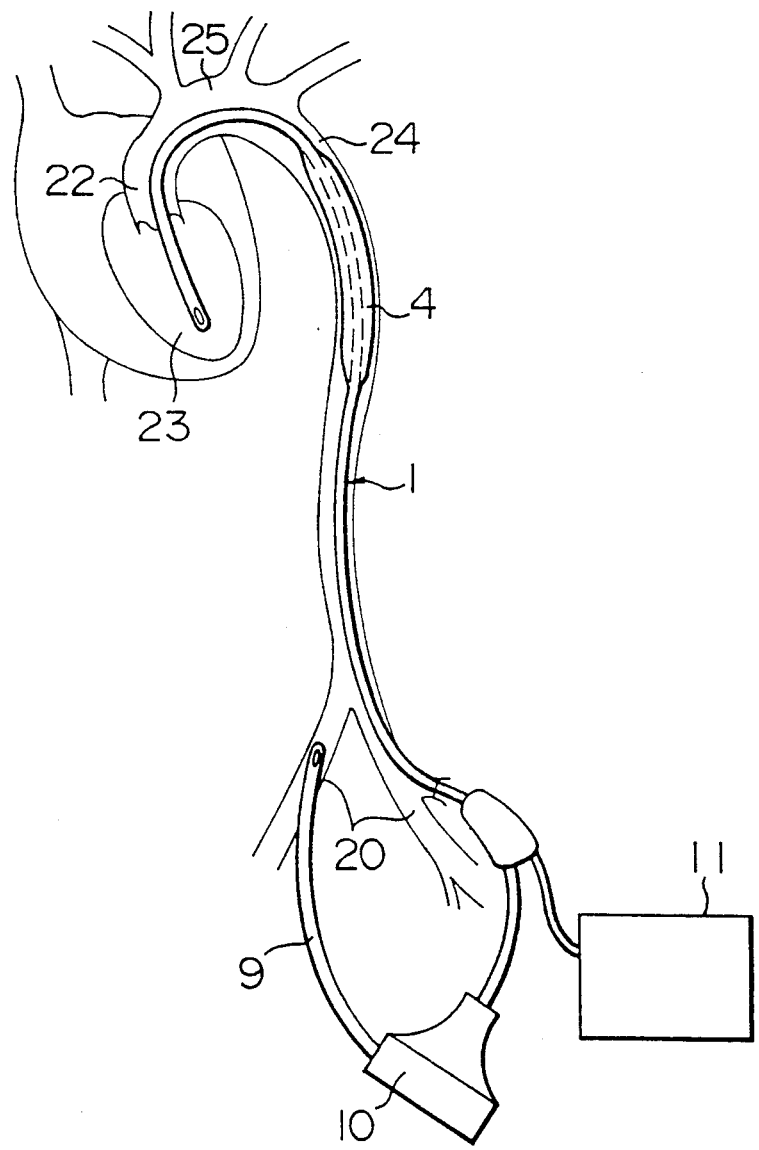

FIGS. 3 and 4 show the cardio assist system in the state of use. The catheter 1 is inserted through a femoral artery such that the distal end of the catheter 1 is disposed into the left ventricule 23 through the aortic valve 22. The blood in the left ventricule 23 is drained through the main lumen 2 and given back to the subclavian artery 21 (FIG. 3) or to the other femoral artery 20 (FIG. 4) by the blood pump 10 through a return line 9. This operation greatly reduces the cardiac work load for pumping the blood and raises the blood pressure to supply the blood to organs such as liver and kidney. The balloon 4 provided outside the catheter 1 is disposed in the descending aorta 24. The balloon 4 is made to inflate and deflate in synchronization with patient's electrocardiogram or arterial pressure wave form so as to produce a pulsatile flow, thus attaining a systolic unloading and diastolic augmentation. It is thus possible to easily provide a left ventricule-aorta by-pass in addition to an IABP. These effects are additive to each other to form a strong assisted circulation by the pulsatile flow.

Figure 5:
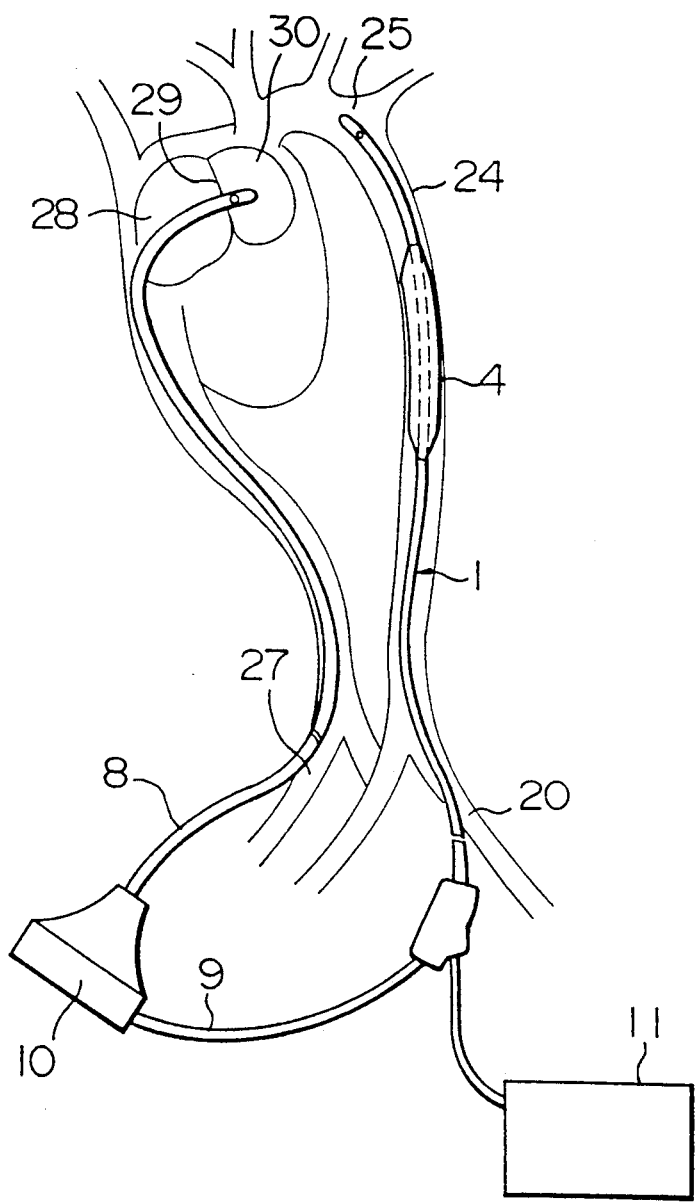

The integrated cardio-assist catheter may be used for giving back the blood. FIG. 5 shows an integrated cardio-assist catheter 1 used as an aortic inflow tube. The catheter 1 is inserted through a femoral artery such that the distal end of the catheter 1 is placed in the aortic arch 25, while the balloon 4 is disposed in the descending aorta 24. On the other hand, a draining tube 8 is inserted into the right atrium 28 through the right external jugular vein or the femoral vein 27 in a manner known per se, with its distal end is disposed in the left atrium 30 through the interatrial septum 29 which has been beforehand punctured by a guide wire. The blood in the left atrium 30 is by-passed to the aorta by the blood pump 10 through a return line 9. According to the present invention, it is thus possible to easily form a strong assisted circulation system in which the left atrium-aorta by-pass and an IABP are combined.

Figure 6:
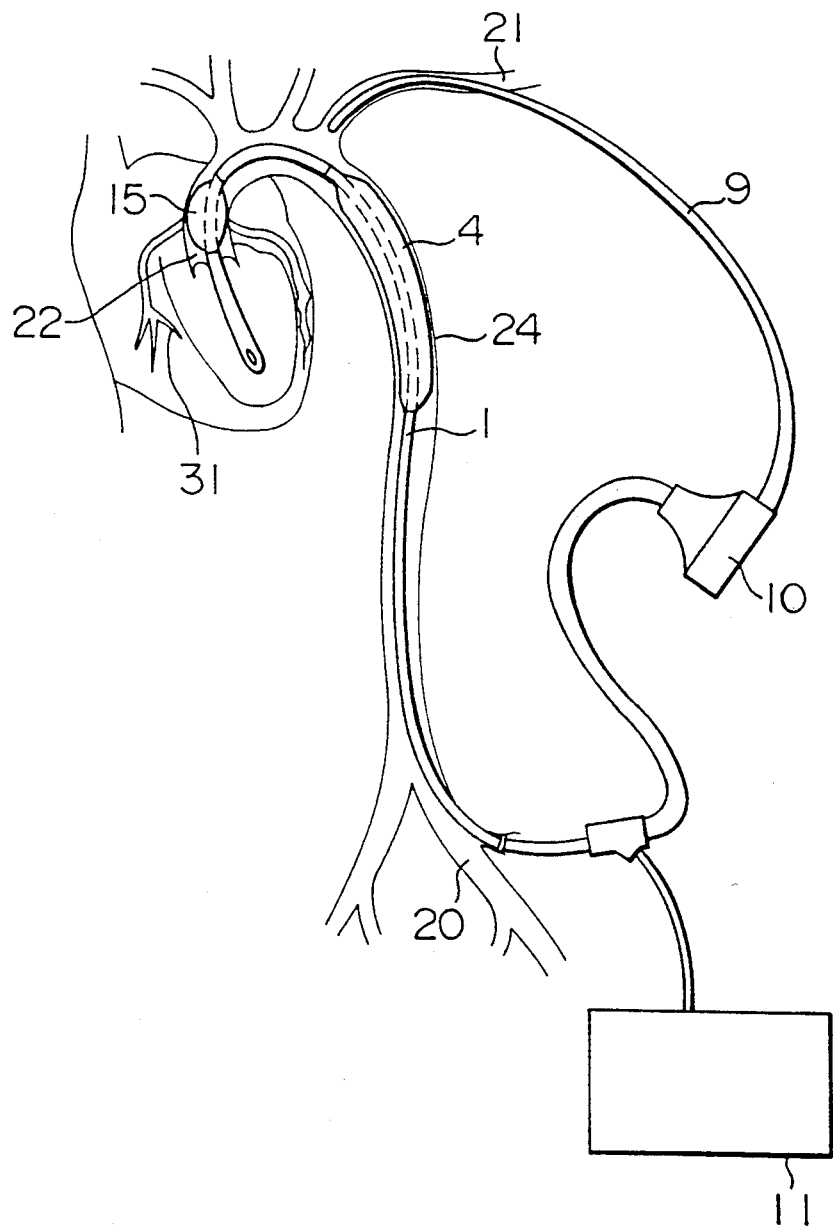
FIG. 6 is an illustration of still another embodiment.

Although the described embodiment has only one balloon, this is not exclusive. For instance, a balloon having two or more chambers therein may be used for attaining a higher precision of control of the blood circulation. It is also possible to use a small balloon 15 which is disposed against the aortic valve 22 in addition to the balloon 4 which is disposed in the descending aorta 24 as shown in FIG. 6. The small balloon 15 is inflated with a slight time delay to the inflation of the balloon 4 so as to raise the coronary arterial pressure step by step, thereby increasing the rate of supply of the blood to the cardiac muscle. In such a case, the sub-lumen 3 is used as the line for supplying the driving gas to the small balloon 15. Although a new gas conduit may be provided to enable the small balloon 15 to operate independently of the balloon 4.

The catheter 1 can be formed by extrusion in a manner known per se to those skilled in this field of art. No limitation is posed on the material of the flexible tube. Thus, polyvinyl chloride, polyurethane, polyamide, polyolefin and silicone resin can suitably be used as the material of the flexible tube. The catheter 1 is in the blood vessel during the operation, so that its surface preferably has antithrombogenicity. To this end, the surface of the catheter may be coated with a blood compatible material such as segmented polyurethane, or a chemical modification is effected on the surface of the catheter material so as to fix an anti-thrombin agent such as heparin or urokinase or drugs which affect platelet reactivity such as dipyridamole and ticlopidine. These methods are selectively used according to conditions.

In order to ensure sufficiently large drainage or supply of the blood, it is necessary that the main lumen 2 forming the blood passage has a sufficiently large cross-sectional area. A too large diameter of the main lumen 2, however, causes the outside diameter of the catheter 1 to be increased, thereby making it difficult to insert the catheter 1 into blood vessel. It is therefore necessary that the diameter of the main lumen 2 is determined to simultaneously meet both these requirements. In order that a catheter 1 is inserted through the femoral artery 20 of an adult patient, the outside diameter of the catheter 1 should be not greater than 7 mm. The length of the catheter 1 must be 0.8 m to 1.0 m in order to reach the left ventricule. The diameter of the main lumen 2 has to be 4 mm or greater, in order to obtain a bypass flow rate of 2.0 litre per minute.

The volume of the balloon 4 in inflated condition is 5 to 40 ml. A suitable balloon is selected according to the position and the dimension in the aorta where the balloon is to be placed. For instance, in case of an adult patient, a balloon having a volume of 35 ml in inflated state is used suitably.

The material of the balloon 4 is required to have durability to withstand more than several millions of inflation/deflation cycles, as well as anti-thrombogenicity. Segmented polyurethane can well meet such a demand. There is no limitation in the type of the segmented polyurethane. It is, however, preferred that the polyurethane has a tensile strength of 200 kg/cm$^2$ and an elongation of 500% or greater.

The diameter of the sub-lumen 3 for supplying a gas for driving the balloon 4 ranges between 1 mm and 3 mm, and preferably between 1.2 mm and 2 mm. A sub-lumen having a diameter of 1 mm or smaller impairs the ability of balloon 4 to respond to the determined cycle for its inflation and deflation. Conversely, a sub-lumen diameter of 3 mm or greater undesirably reduces the cross-sectional area of the main lumen 2, failing to obtain the desired by-pass flow rate. The sub-lumen 3 can have a flattened cross-section shape, provided that the cross-section area is the same. It is also possible to use a plurality of narrow lumens of small diameters as the gas supply conduit.

In order to fully enjoy the merits of the cardio assist system of the invention, it is necessary that the distal end of the integrated cardio assist catheter is guided into the left ventricule accurately, promptly and safely, and that the bleeding is minimized during insertion. When the distal end of the catheter 1 is driven excessively deep into the left ventricule 23, drainage may failed because the drainage port in the end of the catheter is blocked by the wall of the ventricule. On the other hand, an insufficient insertion of the catheter into the left ventricule may result in troubles in that the balloon 4 cannot be held in the desired position to make it inactive or that the catheter 1 comes off the left ventricule to lose the by-passing effect. The catheter 1 has to be advanced along the aortic arch 25 when inserted into the left ventricule 23. If the catheter 1 cannot smoothly turn in the aortic arch, the end of the catheter 1 may dangerously damage the wall of the blood vessel. This may result in a serious failure such as dissection of the aorta. Furthermore, bleeding more blood than necessary during insertion of the catheter burdens the patient too heavily, often affecting the life.

Figure 7:
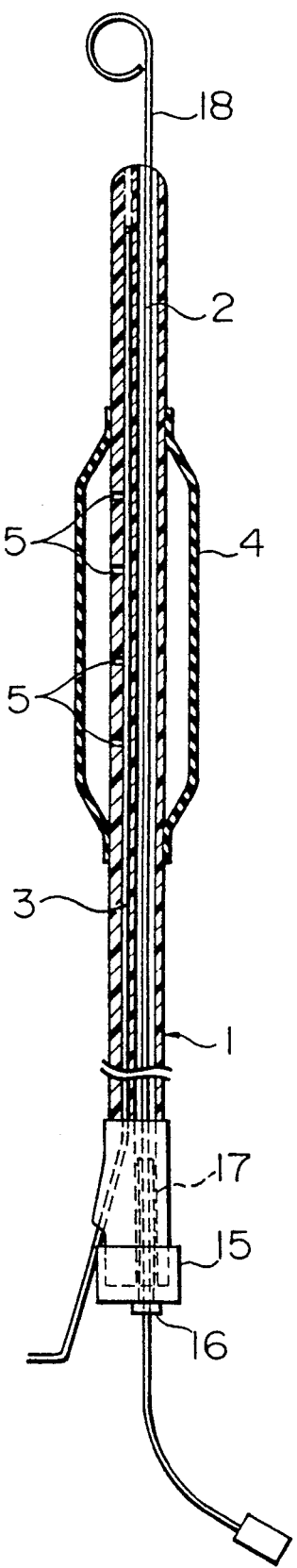
FIG. 7 is an illustration of an integrated cardio-assist catheter in an cardio assist system embodying the present invention, with an insertion device according to an embodiment of the invention.

In order to avoid these problems and enable quick start of assisted circulation, the present invention also provides a device for inserting the integrated cardio-assist catheter. The insertion device has a catheter guiding means having a looped end and adapted to pass through the main lumen of the integrated cardio-assist catheter so as to guide the catheter, and a proximal end plug means having a longitudinal passage and provided with a catheter guiding means insertion portion which is adapted to be connected into the proximal end of the main lumen of the catheter. FIG. 7 shows an embodiment of the insertion device of the present invention assembled together with an integrated cardio-assist catheter.

The proximal end plug means 15 is attached to the proximal end of the catheter 1 such that its rear end blocks the main lumen 2, thus preventing any external escape of the blood which may occur due to reversing of the blood during insertion of the catheter 1 into the artery. The proximal end plug means 15 has a catheter guide means inserting portion 16 through which a catheter guiding means 18 is moved into the main lumen 2 through the passage 17. A catheter for angiography with a looped end, having a diameter of 1 mm to 2.5 mm, preferably 1.5 mm to 2.0 mm, and a length of 1 m to 1.5 m, can suitably be used as the catheter guiding means 18. This, however, is not exclusive and is subject to surgeon's selection. If desired, a guide wire may be inserted into the catheter for angiography. The passage 17 usually has a circular cross-section, with a diameter which is 0.1 mm to 0.5 mm greater than the diameter of the catheter guiding means 18. When the difference in diameter is 0.1 mm or smaller, the clearance between the catheter guiding means 18 and the passage 17 is insufficient so that the catheter guiding means 18 tends to cling on the wall of the passage to impede smooth insertion and extraction. Conversely, when the diameter difference is 0.5 mm or greater, the clearance becomes too large so that the blood reversing in the main lumen 2 undesirably leaks to the exterior.

The length of the passage 17 can be determined freely. However, to afford easy operation of the catheter guiding means 18 and to assure tightness against blood leaks, the passage length is preferably in a range between 20 mm and 40 mm. Too large a length of the passage 17 impedes sliding of the catheter guiding means 18 in the passage 17. Conversely, too small length of passage 17 can permit too much blood leakage through the clearance between the catheter guiding means 18 and the wall of the passage 17.

Thus, operability of the catheter guiding means 18 and prevention of external leaking of blood can be simultaneously attained by suitably adjusting the diameter and length of the passage 17. When absolute prevention of blood leaking is required, it is possible to provide the passage 17 with a check valve and to provide the proximal end plug means 15 with an air vent hole. Any type of check valve presently proposed can be used for the passage 17.

Figure 8:
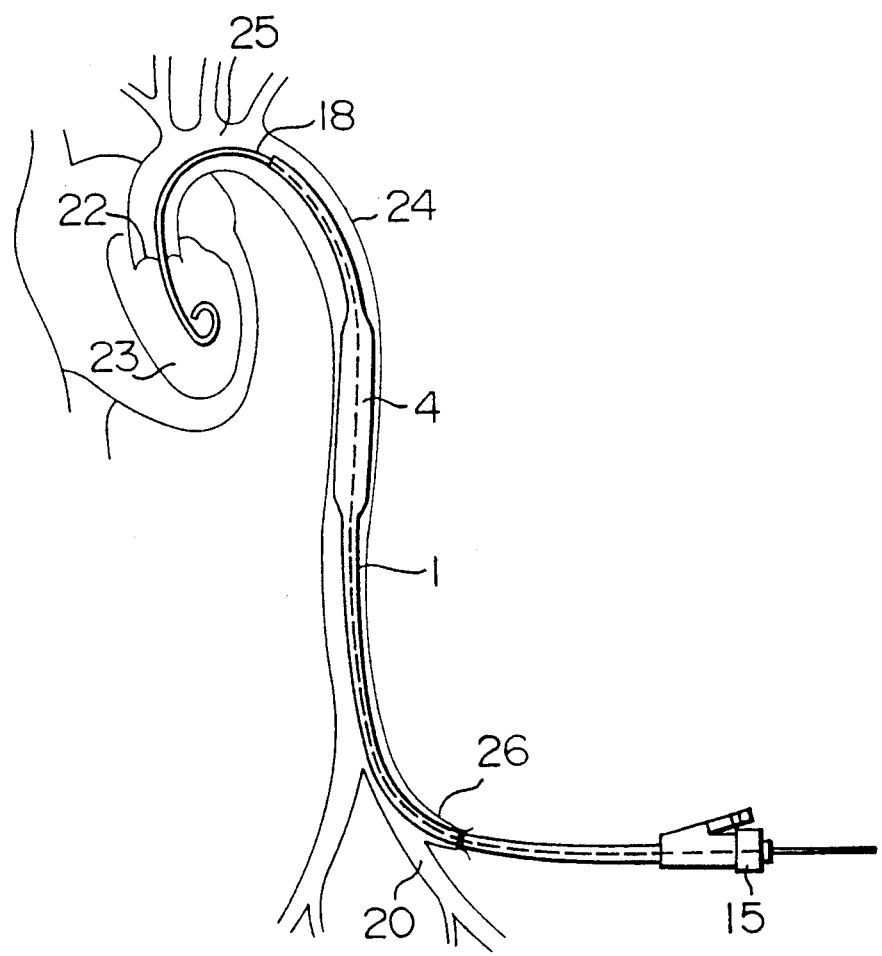
FIG. 8 is an illustration of the manner in which the cardio assist system is installed with an assist of the insertion device.

The advantage of the present invention will be more fully understood from the following description of the manner of use of the insertion device. FIG. 8 illustrates the manner in which a catheter 1 is inserted by using the insertion device in accordance with the present invention. Although the catheter 1 is inserted through a femoral artery in the illustrated embodiment, this is only illustrative and the insertion method described hereinafter can basically be applied when the catheter 1 is inserted through a different portion of the blood system.

As the first step, a catheter guiding means 18 is inserted into and set in the main lumen 2 of the catheter 1, such that the end loop of the catheter guiding means 18 does not project beyond the distal end of the catheter 1.

Subsequently, a femoral artery 20 of the patient is exposed by a surgical operation and an artificial graft 26 is sewed to the portion of the exposed femoral artery where the catheter 1 is to be inserted. The catheter 1 is then inserted into the femoral artery through the artificial graft 26. Reversing of the blood flow takes place in the main lumen 2 due to arterial pressure, but the air in the main lumen 2 is removed through the gap between the wall of the passage 17 and the catheter guiding means 18. If the diameter and the length of the passage 17 have been appropriately determined, only the air is removed from the main lumen 2 and no substantial leak of blood is observed through the above-mentioned gap. When the passage 17 is provided with a check valve, an air vent hole provided in the proximal end plug means 15 is opened to remove the air.

The state or position of the catheter 1 is observed by X-ray fluoro scopy. Upon confirming the arrival of the distal end of the catheter 1 at the inlet of the aortic arch, the catheter guiding means 18 is advanced into the aortic arch 25. The looped end of the catheter guiding means 18 can easily reach the aortic valve 22 along the wall of the aortic arch. A further advance of the catheter guiding means 18 causes the end of this means to reach interior of the left ventricule 23.

When the reach of the end of the catheter guiding means 18 to the interior of the left ventricule 23 is detected through the X-ray fluoroscopic observation, the catheter 1 is moved ahead along the catheter guiding means 18. When the end of the catheter 1 has reached the left ventricule 23, the catheter guiding means 18 is extracted and the proximal end plug means 15 is detached after the proximal end of the catheter 1 is clamped by a tube clamp. Then, the proximal end of the main lumen 2 is connected to the circulation circuit, thus completing the connecting operation.

Thus, the insertion device of the present invention enables an easy, safe and prompt insertion of the cardio assist system. The described method can be applied also to percutaneous catheterization relying upon Seldinger method. In such a case, the installing time can be further shortened.

As has been described, it is possible to quickly and easily form a strong assisted circulation by combining an integrated cardio-assist catheter, a balloon driver and a blood pump. In addition, the integrated cardio-assist catheter can be installed by minimal surgical procedure. At the same time, the left ventricule is greatly unburdened while the blood flow rate in coronary artery is increased. Thus, the present invention is very effective as treating system for those suffering from intractable cardiac failure.

What is claimed is:

1. A cardio assist system comprising:

a catheter for insertion from one femoral artery into a left ventricle through an aorta, said catheter including a main lumen, a sub-lumen which is sealed at a distal end thereof, and a distal end of said catheter having an open end of said main lumen for retention in said left ventricle;

a balloon means gas-tightly attached and surrounding a distal end portion of said catheter to define therebetween a balloon chamber, for inflation and deflation in a descending aorta;

a plurality of apertures provided in said distal end portion of said catheter for communication between said balloon chamber and said sub-lumen;

a balloon driver means connected to a proximal end of said sub-lumen for supplying a drive gas to and discharging it from said balloon chamber through said sub-lumen and said apertures, said balloon driver means being synchronized with a patient's electrocardiogram or arterial pressure waveform so as to inflate and deflate said balloon means to produce a pulsatile flow; and a blood pump connected in suction to said open end of said main lumen at a proximal end of said main lumen of said catheter;

a return line connected to said blood pump for retention in another femoral artery or subclavian artery;

said blood pump constituting means for selectively sucking blood from said left ventricle through said main lumen and thereafter pumping said blood through said return line to said another femoral artery or subclavian artery.

2. A cardio assist system according to claim 1, wherein said catheter further comprises a second sub-lumen opened at said distal end of said catheter, and a branch tube branching from a proximal end of said second sub-lumen and provided at an end thereof with a passage switching cock.

3. A cardio assist system according to claim 1, wherein said balloon means has a plurality of balloons, and said balloon driver means supplies and discharges the gas sequentially to said plurality of balloons, thereby repeating inflation and deflation of said plurality of balloons with a time phase difference from one another.

4. A cardio assist system according to claim 2, wherein said balloon means has a plurality of balloons, and said balloon drive means supplies and discharges gas sequentially to said plurality of balloons, thereby repeating inflation and deflation of said plurality of balloons with a time phase difference from one another.

* * * * *